(12) United States Patent
McConville et al.

(10) Patent No.: US 10,436,758 B2
(45) Date of Patent: Oct. 8, 2019

(54) METHOD AND APPARATUS FOR DETERMINING AN ULTRAVIOLET (UV) CURE LEVEL

(71) Applicant: Xerox Corporation, Norwalk, CT (US)

(72) Inventors: Paul McConville, Webster, NY (US); Jason M. LeFevre, Penfield, NY (US); Douglas K. Herrmann, Webster, NY (US); Michael J. Levy, Webster, NY (US); Seemit Praharaj, Webster, NY (US)

(73) Assignee: Xerox Corporation, Norwalk, CT (US)

(*) Notice: Subject to any disclaimer, the term of this patent is extended or adjusted under 35 U.S.C. 154(b) by 165 days.

(21) Appl. No.: 15/625,783

(22) Filed: Jun. 16, 2017

(65) Prior Publication Data

US 2018/0364202 A1    Dec. 20, 2018

(51) Int. Cl.
| | |
|---|---|
| *G01N 29/44* | (2006.01) |
| *C08J 3/24* | (2006.01) |
| *C09D 11/101* | (2014.01) |
| *G01N 29/24* | (2006.01) |
| *G01N 25/00* | (2006.01) |
| *G01N 33/44* | (2006.01) |

(52) U.S. Cl.
CPC .............. *G01N 29/44* (2013.01); *C08J 3/248* (2013.01); *C09D 11/101* (2013.01); *G01N 25/00* (2013.01); *G01N 29/2418* (2013.01); *G01N 29/2431* (2013.01); *G01N 29/4427* (2013.01); *G01N 33/442* (2013.01); *C08J 2300/00* (2013.01); *G01N 2291/0251* (2013.01); *G01N 2291/02818* (2013.01); *G01N 2291/02827* (2013.01); *G01N 2291/0423* (2013.01)

(58) Field of Classification Search
CPC .... G01N 29/44; G01N 25/00; G01N 29/2418; G01N 2291/02818; G01N 2291/02827; G01N 2291/04; C08J 3/248; C08J 2300/00; C09D 11/101
See application file for complete search history.

(56) References Cited

U.S. PATENT DOCUMENTS

| | | | | |
|---|---|---|---|---|
| 5,302,627 | A * | 4/1994 | Field .................... | C08F 2/46 522/13 |
| 5,633,711 | A * | 5/1997 | Nelson ............... | G01B 11/0666 356/318 |
| 5,776,409 | A * | 7/1998 | Almquist ............... | B29C 64/40 118/407 |
| 6,061,134 | A * | 5/2000 | Jensen ................... | G01J 3/44 356/451 |
| 7,987,717 | B2 * | 8/2011 | Casagrande ....... | G01N 29/2418 73/150 R |
| 8,189,189 | B1 * | 5/2012 | Herendeen .............. | G01J 3/501 356/300 |

(Continued)

*Primary Examiner* — Lisa M Caputo
*Assistant Examiner* — Philip L Cotey (57) ABSTRACT

A method for determining an ultraviolet (UV) cure level of a material is disclosed. For example, the method includes receiving an object with the material that is cured via a UV light source, controlling a heat source to heat the material, measuring a parameter of the material in response to the heat, determining the UV cure level of the material based on the parameter that is measured and a predefined response of the material at a temperature associated with the heat, and generating a signal to display the UV cure level in response to the determining.

20 Claims, 4 Drawing Sheets

(56) References Cited

U.S. PATENT DOCUMENTS

| | | | | |
|---|---|---|---|---|
| 8,876,513 B2* | 11/2014 | Lim | ................. | B29C 67/0059 425/174.4 |
| 9,796,862 B2* | 10/2017 | Morita | ................. | C09D 11/101 |
| 9,962,882 B2* | 5/2018 | Kritchman | ................. | G06F 17/50 |
| 10,086,563 B2* | 10/2018 | Hattori | ................. | B29C 43/18 |
| 2001/0038890 A1* | 11/2001 | Buazza | ................. | B29D 11/00442 428/1.1 |
| 2002/0054975 A1* | 5/2002 | Hayashida | ................. | B32B 3/02 428/64.4 |
| 2003/0074095 A1* | 4/2003 | Neubauer | ................. | G01B 11/28 700/117 |
| 2003/0083771 A1* | 5/2003 | Schmidt | ................. | B33Y 30/00 700/119 |
| 2003/0100119 A1* | 5/2003 | Weinberg | ................. | C08F 4/7081 436/37 |
| 2003/0119199 A1* | 6/2003 | Wolf | ................. | C08F 279/04 436/164 |
| 2004/0058058 A1* | 3/2004 | Shchegolikhin | ................. | B41M 3/14 427/7 |
| 2006/0044555 A1* | 3/2006 | Wang | ................. | A61C 19/003 356/301 |
| 2008/0240763 A1* | 10/2008 | Casagrande | ................. | G01N 29/2418 399/67 |
| 2009/0267269 A1* | 10/2009 | Lim | ................. | B29C 67/0059 264/401 |
| 2009/0323056 A1* | 12/2009 | Yun | ................. | G01J 3/26 356/301 |
| 2010/0208006 A1* | 8/2010 | Selinfreund | ................. | G01N 35/1016 347/68 |
| 2014/0002530 A1* | 1/2014 | Thompson | ................. | B41M 7/0081 347/16 |
| 2014/0002558 A1* | 1/2014 | Ramesh | ................. | B41J 11/002 347/102 |
| 2015/0298166 A1* | 10/2015 | Poullos | ................. | B05D 3/06 427/8 |
| 2016/0121599 A1* | 5/2016 | Bauer | ................. | B41F 15/08 118/704 |
| 2016/0375676 A1* | 12/2016 | Ritchie | ................. | B33Y 80/00 428/29 |
| 2017/0151722 A1* | 6/2017 | Prasad | ................. | B29C 67/00 |
| 2017/0283655 A1* | 10/2017 | Kenney | ................. | B29C 64/106 |

* cited by examiner

METHOD AND APPARATUS FOR DETERMINING AN ULTRAVIOLET (UV) CURE LEVEL

The present disclosure relates generally to three dimensional (3D) printing and, more particularly, to a method and apparatus for determining a UV cure level of a material.

BACKGROUND

Additive printing, also referred to as 3D printing, has emerged as an innovative manufacturing technology. 3D printing promises unprecedented benefits to manufacturers such as reduced cost of production and expedited development and customization.

3D printing operates by adding a layer of a build material in accordance with an outline or shape of the printed part. The layer may be cured, for example, by an ultra violet curing light. The process of adding build material and curing may be repeated layer by layer until the printed part is completed. The printing may be controlled by a computer.

If the material is not fully cured, the material may not have a proper finish, exhibit undesirable qualities, not adhere properly, and the like. Currently, there is not an efficient method to determine whether the material that is printed is fully cured.

SUMMARY

According to aspects illustrated herein, there are provided a method, non-transitory computer readable medium and apparatus for determining an ultraviolet (UV) cure level of a material. One disclosed feature of the embodiments is a method that receives an object with material that is cured via a UV light source, controls a heat source to heat the material, measures a parameter of the material in response to the heat, determines the UV cure level of the material based on the parameter that is measured and a predefined response of the material at a temperature associated with the heat and generates a signal to display the cure level in response to the determining.

Another disclosed feature of the embodiments is a non-transitory computer-readable medium having stored thereon a plurality of instructions, the plurality of instructions including instructions which, when executed by a processor, cause the processor to perform operations that receive an object with material that is cured via a UV light source, control a heat source to heat the material, measure a parameter of the material in response to the heat, determine the UV cure level of the material based on the parameter that is measured and a predefined response of the material at a temperature associated with the heat and generate a signal to display the cure level in response to the determining.

Another disclosed feature of the embodiments is an apparatus comprising a processor and a computer-readable medium storing a plurality of instructions which, when executed by the processor, cause the processor to perform operations that receive an object with material that is cured via a UV light source, control a heat source to heat the material, measure a parameter of the material in response to the heat, determine the UV cure level of the material based on the parameter that is measured and a predefined response of the material at a temperature associated with the heat and generate a signal to display the cure level in response to the determining.

BRIEF DESCRIPTION OF THE DRAWINGS

The teaching of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

The present disclosure broadly discloses a method and apparatus for determining an ultraviolet (UV) cure level of a material. As discussed above, 3D printing operates by adding a layer of a build material in accordance with an outline or shape of the printed part. The layer may be cured, for example, by an ultra violet curing light. The process of adding build material and curing may be repeated layer by layer until the printed part is completed. The printing may be controlled by a computer.

If the material is not fully cured, the material may not have a proper finish, exhibit undesirable qualities, not adhere properly, and the like. Currently, there is not an efficient method to determine whether the material that is printed is fully cured.

Embodiments of the present disclosure provide an apparatus and a method to perform a novel non-destructive technique for evaluating the cure level of a UV cured material. The method of the present disclosure applies heat to a portion or a point of the material to create Rayleigh waves in the material. Properties of the Rayleigh waves may be measured and compared to known values of the properties associated with materials that are known to be fully cured. If the measured properties match the known values of the properties then the material may be deemed to be fully cured.

Figure 1:
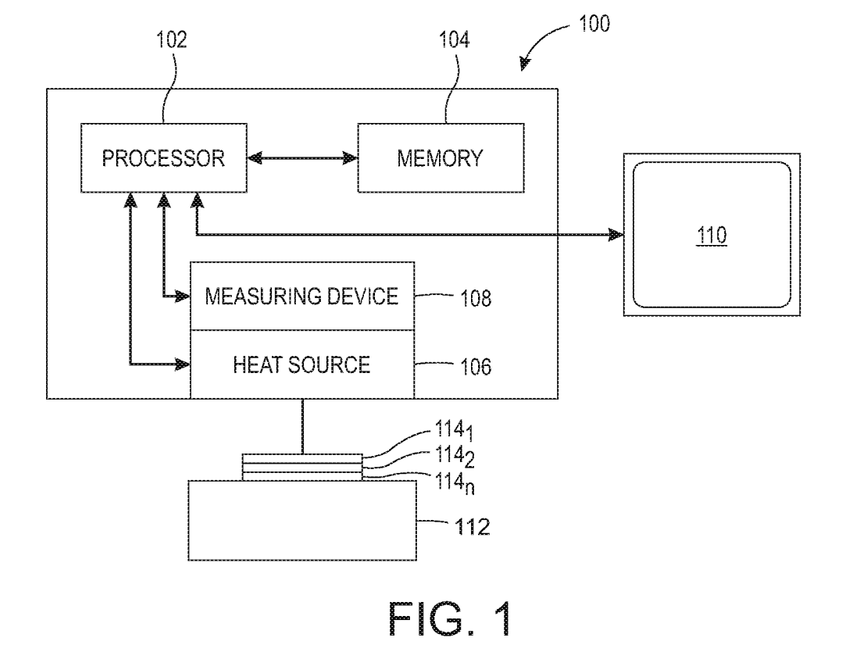
FIG. 1 illustrates a block diagram of an example apparatus of the present disclosure.

FIG. 1 illustrates an example apparatus 100 of the present disclosure. In one embodiment, the apparatus 100 may include a processor 102, a memory 104, a heat source 106, and a measuring device 108. In one embodiment, the apparatus 100 may be part of a three dimensional (3D) printing apparatus or device. For example, the apparatus 100 may be positioned along a print path of an object 112 in the 3D printing apparatus or device.

In one embodiment, the processor 102 may be communicatively coupled to the memory 104, the heat source 106, and the measuring device 108. The processor 102 may control operation of the heat source 106 and the measuring device 108. The processor 102 may collect data measured by the measuring device 108 and process the data along with data that is stored in the memory 104.

In one embodiment, the heat source 108 may be a point source. For example, the heat source 108 may be a laser. The heat source 108 may heat a material a point on a top layer of a material $114_1$ that has a plurality of layers of material $114_1$ to $114_n$ (hereinafter also referred to as a material 114 or materials 114) that is printed on the object 112.

In one embodiment, the materials 114 may be a UV curable material or ink that can be added or printed in a 3D printing process. In one embodiment, the materials 114 may be a photopolymeric material. In one embodiment, the materials $114_1$ to $114_n$ may be the same material for each layer or may be different materials for each layer, or may have some layers with the same type material 114 and some layers with a different type material 114.

In one embodiment, the heat source 108 may heat the top layer of the material $114_1$ at a temperature that is sufficient to induce Rayleigh waves in the top layer of the material $114_1$ without melting, or effecting, the top layer of the material $114_1$. In one example, the temperature may be a temperature within a range of approximately 30 degrees Celsius (° C.) to 200° C. In one embodiment, a temperature of approximately 75° C. can be used.

In one embodiment, the temperature that is used may be also a function of a time range in which the material 114 has to change temperature (e.g., to go from nominal/room temperature to a target temperature). In one embodiment, a time range may be approximately 10 microseconds (μs) to 100 μs. Thus, in one embodiment, the parameters of the time change, or Δtime, and a temperature change, or Δtemp, may give the best conditions in the material 114 for a Rayleigh wave to be generated.

In one embodiment, as noted above, the heat source 108 may apply heat to a point or a small area of the top layer of the material $114_1$. In other words, the heat source 108 does not heat the entire top layer of the material $114_1$ or all layers of the materials $114_1$ to $114_n$.

In one embodiment, the measuring device 108 may be any type of device that can measure physical properties or changes in the top layer of the material $114_1$ caused by the heat applied by the heat source 106. In one embodiment, the measuring device 108 may be an interferometer. The measuring device may measure one or more parameters of the material 114 in response to the heat that is applied.

As discussed above, the heat may cause Rayleigh waves in the top layer of the material $114_1$. The Rayleigh waves may have properties that are associated with how fast the waves move and how quickly the waves dissipate radially outward from the point that receives the heat. How fast the waves move may be measured as a storage modulus value. How quickly the waves dissipate radially outward may be measured as a loss modulus value. The values of the storage modulus value and the loss modulus value may vary as a function of a type of material, a cure level of the material, and a temperature that is applied to the material.

In one embodiment, the memory 104 may be a computer readable storage medium that stores known storage modulus values and known loss modulus values for different material at different temperatures. For example, different materials may be cured and the full cure may be verified using a chemical leaching process. The material may be determined to be fully cured when additional UV radiation causes no additional monomer conversion within the material. This may be verified by weighing a part with the cured material and then dissolving the cured material in cyclohexane to leach out all of the uncured monomers. The part may be removed after 24 hours, dried, and weighed to calculate the uncured monomers lost via leaching. The heat source 106 may be applied to the material that has been verified to be fully cured. The storage modulus values and the loss modulus values may then be measured and charted for different materials.

Figure 2:
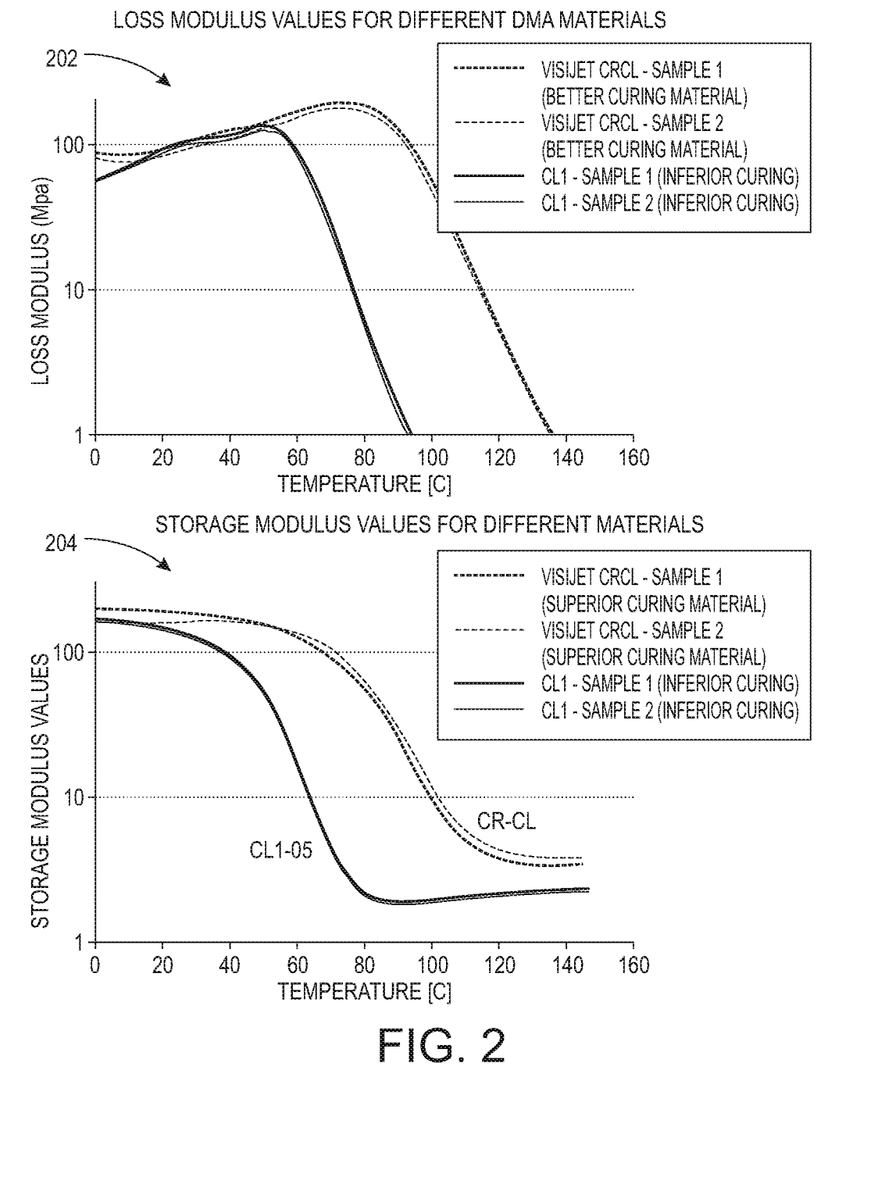
FIG. 2 illustrates example graphs that illustrate loss modulus and storage modulus profiles at different temperatures of different materials.

FIG. 2 illustrates a graph 202 of loss modulus values and a graph 204 of storage modulus values for different materials. The graph 202 includes the loss modulus values at different temperatures for two different materials (e.g., a first material (e.g., Visijet CRCL) and a second material (e.g., CL1). The first material used in the graph 202 may have a better cure, or may be cured more completely, than the second material. As can be seen in the graph 202, each material has a different profile of loss modulus values at different temperatures. In addition, the loss modulus values at different temperatures for each material is relatively consistent. The loss modulus and the storage modulus may be measured in mega-Pascals (MPa).

Similarly, the graph 204 includes the storage modulus values at different temperatures for the same two different materials. As can be seen in the graph 204, each material has a different profile of storage modulus values at different temperatures. In addition, the storage modulus values at different temperatures for each material is relatively consistent.

The measured storage modulus values and the loss modulus values may be compared to the known values in the predefined responses shown in the graph 202 and 204 and stored in the memory 104. In one embodiment, the material 114 may be determined to be fully cured when the measured storage modulus value and the measured loss modulus value of the material 114 matches the known values for the corresponding material in the graph 202 and the graph 204. In one embodiment, the match may be within a predefined threshold. For example, the predefined threshold may be within +/−1%, +/−5%, +/−10%, and the like. In another example, the predefined threshold may be a numerical value, e.g., +/−5, +/−10, +/−20, and the like.

In one embodiment, the material 114 may be determined to be not fully cured, or insufficiently cured, when the measured storage modulus value and the measured loss modulus value of the material 114 does not match the known values for the corresponding material in the graph 202 and the graph 204. In one embodiment, the measured storage modulus value and the measured loss modulus value of the material 114 may be determined to not match the known values for the corresponding material in the graph 202 and the graph 204 when the measured storage modulus value and the measured loss modulus value are different by an amount that is greater than the predefined threshold.

In one embodiment, the determined cure level may be displayed on a display 110. For example, the processor 102 may generate a signal and output a message that is displayed on the display 110. In one embodiment, if the cure level is determined to be fully cured, then the object 112 may be removed (e.g., from a 3D printer). In one embodiment, if the cure level is determined to not be fully cured, or insufficiently cured, then the object 112 may be re-processed to print additional material 114 on the object 112 or perform additional curing on the materials 114. For example, the object 112 may be on a trolley or movable platform of a 3D printer that moves the object 112 back in front of an array of printheads or a UV curing light source for additional curing.

As a result, the apparatus 100 provides a novel non-destructive testing technique to evaluate a cure level of materials 114. For example, the apparatus 100 may automatically determine whether a UV curable ink that is printed on the object 112 is fully cured. The apparatus 100 may be implemented in a 3D printer or print system to allow the 3D printer to determine the cure level of the printed material 114 in-line.

Without the apparatus 100, the object 112 may have to be removed and analyzed off-line. If the materials 114 is not fully cured, the object 112 would have to be returned to the 3D printer and cured again to complete the curing and the object 112 would be analyzed off-line again. This process may be inefficient and the apparatus 100 provides a more efficient process for evaluating a cure level of materials (e.g., UV curable inks).

Figure 3:
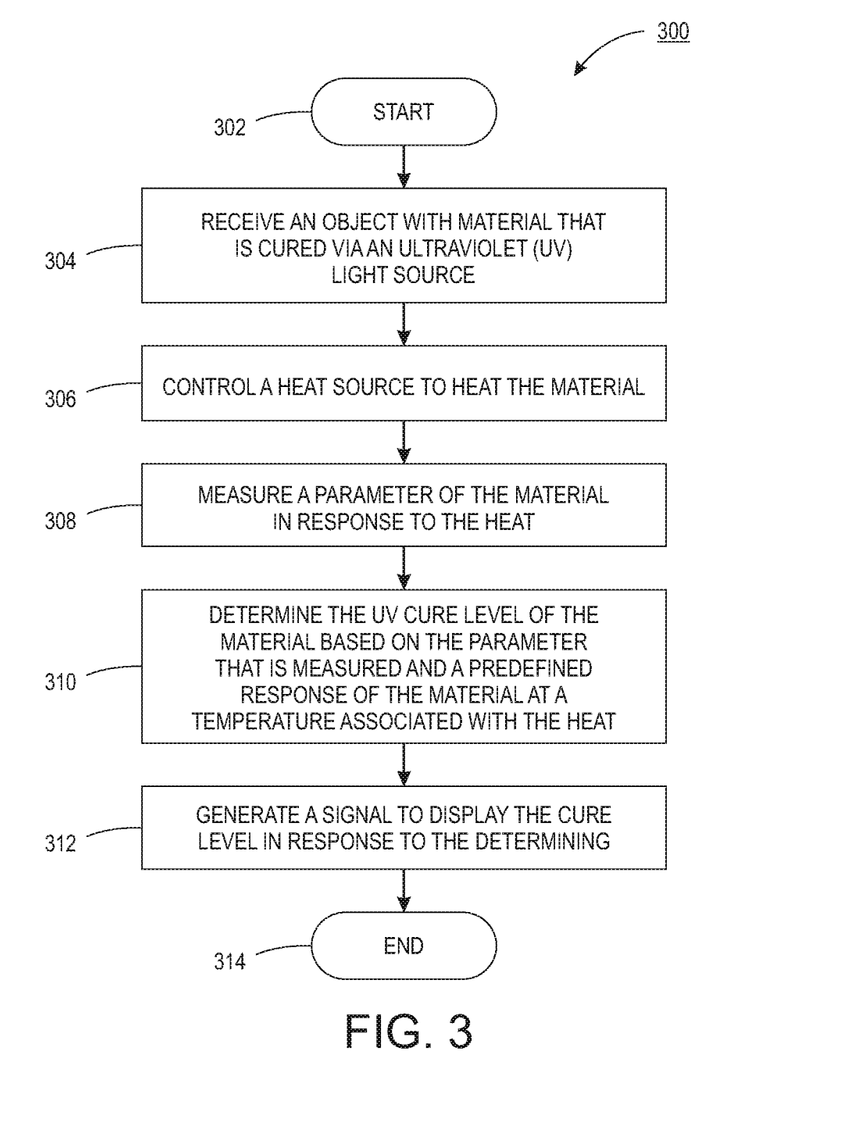
FIG. 3 illustrates a flowchart of an example method for determining a UV cure level of a material of the present disclosure.
Figure 4:
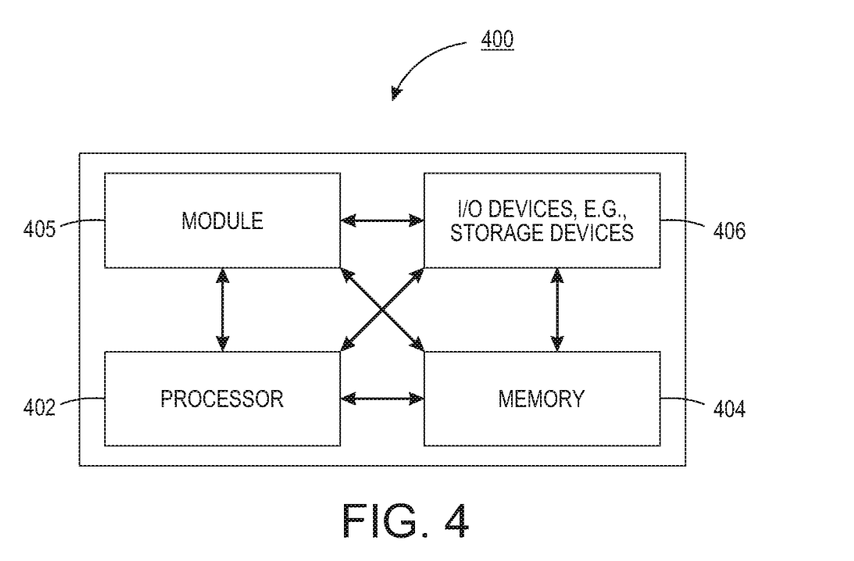
FIG. 4 illustrates a high-level block diagram of an example computer suitable for use in performing the functions described herein.

FIG. 3 illustrates a flowchart of an example method 300 for determining a UV cure level of a material. In one embodiment, one or more steps or operations of the method 300 may be performed by the apparatus 100 or a computer that controls operation of the apparatus 100 as illustrated in FIG. 4 and discussed below.

At block 302, the method 300 begins. At block 304, the method 300 receives an object with material that is cured via a UV light source. For example, the object may be passed through a 3D printer that applies UV curable material (e.g., a UV curable ink, photopolymeric material, and the like). The object may be placed on a platform of an apparatus that performs the method 300. In one embodiment, the apparatus that performs the method 300 may be part of a 3D printer or print system and the object may be moved via a movable platform.

At block 306, the method 300 controls a heat source to heat the material. In one embodiment, the object may be positioned in the path of the heat source such that a point of the material may be heated. For example, the object may be to a side of the heat source that emits the heat in a lateral direction, the object may be below the heat source that emits the heat in a downward direction, or the object may be above the heat source that emits the heat in an upward direction.

As noted above, the heat source provides a point source. For example, the heat source may be a laser. As a result, a point, a portion, a sub-region, or less than all of the surface area of the material, may be heated. In other words, the heat source does not apply heat around the entire material similar to an oven. The heat source may provide heat at a temperature that is sufficient to induce Rayleigh waves on a top layer of the material without melting, or effecting, the top layer of the material. In one example, the temperature may be a temperature within a range of approximately 30 degrees Celsius (° C.) to 200° C. In one embodiment, a temperature of approximately 75° C. can be used.

In addition, as noted above, the temperature that is used may be also a function of a time range in which the material 114 has to change temperature (e.g., to go from nominal/room temperature to a target temperature). In one embodiment, a time range may be approximately 10 microseconds (μs) to 100 μs. Thus, in one embodiment, the parameters of the time change, or Δtime, and a temperature change, or Δtemp, may give the best conditions in the material 114 for a Rayleigh wave to be generated.

At block 308, the method 300 measures a parameter of the material in response to the heat. In one embodiment, the parameter may be one or more properties associated with the Rayleigh waves that are induced by the heat applied to the material. For example, the properties may include a storage modulus and a loss modulus. A storage modulus value may measure how fast the waves move radially outward from the point that is heated. A loss modulus value may measure how quickly the waves dissipate radially outward.

In one embodiment, any measuring device that can analyze and measure the physical properties or changes in the top layer of the material caused by the heat may be used to measure the parameter. In one embodiment, an interferometer may be used.

At block 310, the method 300 determines the UV cure level of the material based on the parameter that is measured and a predefined response of the material at a temperature associated with the heat. For example, the predefined response of the material at the temperature associated with the heat may be stored as pre-defined graphs in memory. A graph for each one of a plurality different materials that may be used in the 3D printer may be stored in memory. Each graph for each material that is known to be fully cured may have a different response and profile shown in a respective graph at different temperatures.

In one embodiment, the value of the parameter of the material that is measured may be compared to the known value of the parameter in the pre-defined graph for the same material. If the values match, then the material may be determined to be fully cured. If the values do not match, then the material may be determined to not be fully cured, or insufficiently cured indicating that additional material requires additional UV curing.

For example, the storage modulus value and the loss modulus value of a Rayleigh wave caused by heat that is applied to a material may be measured, as described above. The storage modulus value and the loss modulus value may be compared to a graph that provides known storage modulus values and known loss modulus values at various temperature values. If the storage modulus value and the loss modulus value match the known storage modulus value and known loss modulus value at a temperature of the heat applied to the material, then the material may be deemed to be fully cured.

In one embodiment, a predefined threshold may be used. For example, the method 300 may determine that the value of the parameter matches the predefined response of the material at the temperature when the values are within the predefined threshold. Similar, the method 300 may determine that the value of the parameter does not match the predefined response of the material at the temperature when the values are outside of the predefined threshold. For example, the predefined threshold may be within +/−1%, +/−5%, +/−10%, and the like. In another example, the predefined threshold may be a numerical value, e.g., +/−5, +/−10, +/−20, and the like.

At block 312, the method 300 generates a signal to display the cure level in response to the determining. For example, a signal that indicates whether the cure level is fully cured or insufficiently cured may be transmitted to be shown on the display. Thus, method 300 may generate an output based on the determination of the cure level that can be provided to a display (e.g., a monitor or touch screen interface).

In one embodiment, the object may be returned to a curing station of a 3D printer in response to the signal if the cure level is determined to be insufficient. In another embodiment, the object may be moved to a removal station of the 3D printer, or a home location for the object to be safely removed in response to the signal if the cure level is determined to be fully cured. At block 314, the method 300 ends.

It should be noted that the blocks in FIG. 3 that recite a determining operation or involve a decision do not necessarily require that both branches of the determining operation be practiced. In other words, one of the branches of the determining operation can be deemed as an optional step. In addition, one or more steps, blocks, functions or operations of the above described method 300 may comprise optional steps, or can be combined, separated, and/or performed in a different order from that described above, without departing from the example embodiments of the present disclosure.

FIG. 4 depicts a high-level block diagram of a computer that is dedicated to perform the functions described herein. As depicted in FIG. 4, the computer 400 comprises one or more hardware processor elements 402 (e.g., a central processing unit (CPU), a microprocessor, or a multi-core processor), a memory 404, e.g., random access memory (RAM) and/or read only memory (ROM), a module 405 for determining a UV cure level of a material, and various input/output devices 406 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the computer may employ a plurality of processor elements. Furthermore, although only one computer is shown in the figure, if the method(s) as discussed above is implemented in a distributed or parallel manner for a particular illustrative example, i.e., the steps of the above method(s) or the entire method(s) are implemented across multiple or parallel computers, then the computer of this figure is intended to represent each of those multiple computers. Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented.

It should be noted that the present disclosure can be implemented in software and/or in a combination of software and hardware, e.g., using application specific integrated circuits (ASIC), a programmable logic array (PLA), including a field-programmable gate array (FPGA), or a state machine deployed on a hardware device, a computer or any other hardware equivalents, e.g., computer readable instructions pertaining to the method(s) discussed above can be used to configure a hardware processor to perform the steps, functions and/or operations of the above disclosed methods. In one embodiment, instructions and data for the present module or process 405 for determining a UV cure level of a material (e.g., a software program comprising computer-executable instructions) can be loaded into memory 404 and executed by hardware processor element 402 to implement the steps, functions or operations as discussed above in connection with the example method 300. Furthermore, when a hardware processor executes instructions to perform "operations," this could include the hardware processor performing the operations directly and/or facilitating, directing, or cooperating with another hardware device or component (e.g., a co-processor and the like) to perform the operations.

The processor executing the computer readable or software instructions relating to the above described method(s) can be perceived as a programmed processor or a specialized processor. As such, the present module 405 for determining a UV cure level of a material (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. More specifically, the computer-readable storage device may comprise any physical devices that provide the ability to store information such as data and/or instructions to be accessed by a processor or a computing device such as a computer or an application server.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method for determining an ultraviolet (UV) cure level of a material, comprising:
    moving, by a processor, a platform to receive an object with a plurality of layers of the material that is printed in a three-dimensional printer and is cured via a UV light source;
    controlling, by the processor, a heat source to heat a point on a top layer of the material;
    measuring, by the processor, a parameter of the material in response to the heat;
    determining, by the processor, the UV cure level of the material based on the parameter that is measured and a predefined response of the material at a temperature associated with the heat; and
    generating, by the processor, a signal to display the UV cure level in response to the determining.

2. The method of claim 1, wherein the material comprises a photopolymeric material.

3. The method of claim 1, wherein the heat source comprises a point source.

4. The method of claim 1, wherein the measuring is performed by an interferometer.

5. The method of claim 1, wherein the parameter comprises one or more properties of a Rayleigh wave generated in the material in response to the heat.

6. The method of claim 5, wherein the one or more properties comprise a loss modulus value and a storage modulus value.

7. The method of claim 6, wherein the predefined response comprises a graph of the loss modulus value of the material that is known to be fully cured at a plurality of different temperatures.

8. The method of claim 6, wherein the predefined response comprises a graph of the storage modulus value of the material that is known to be fully cured at a plurality of different temperatures.

9. The method of claim 1, wherein the UV cure level of the material comprises a fully cured level when the parameter that is measured matches the predefined response of the material at the temperature within a predefined threshold.

10. The method of claim 1, wherein the UV cure level of the material comprises an insufficient cured level when the parameter that is measured does not match the predefined response of the material at the temperature within a predefined threshold.

11. A non-transitory computer-readable medium storing a plurality of instructions, which when executed by a processor, cause the processor to perform operations for determining an ultraviolet (UV) cure level of a material, the operations comprising:
    moving a platform to receive an object with a plurality of layers of the material that is printed in a three-dimensional printer and is cured via a UV light source;
    controlling a heat source to heat a point on a top layer of the material;

measuring a parameter of the material in response to the heat;

determining the UV cure level of the material based on the parameter that is measured and a predefined response of the material at a temperature associated with the heat; and generating a signal to display the UV cure level in response to the determining.

12. The non-transitory computer-readable medium of claim 11, wherein the material comprises a photopolymeric material.

13. The non-transitory computer-readable medium of claim 11, wherein the heat source comprises a point source.

14. The non-transitory computer-readable medium of claim 11, wherein the measuring is performed by an interferometer.

15. The non-transitory computer-readable medium of claim 11, wherein the parameter comprises one or more properties of a Rayleigh wave generated in the material in response to the heat.

16. The non-transitory computer-readable medium of claim 15, wherein the one or more properties comprise a loss modulus value and a storage modulus value.

17. The non-transitory computer-readable medium of claim 16, wherein the predefined response comprises a graph of the loss modulus value of the material that is known to be fully cured at a plurality of different temperatures.

18. The non-transitory computer-readable medium of claim 16, wherein the predefined response comprises a graph of the storage modulus value of the material that is known to be fully cured at a plurality of different temperatures.

19. The non-transitory computer-readable medium of claim 11, wherein the UV cure level of the material comprises a fully cured level when the parameter that is measured matches the predefined response of the material at the temperature within a predefined threshold.

20. A method for determining an ultraviolet (UV) cure level of a material, comprising:

moving, by a processor, a platform to receive an object with a plurality of layers of the material that is printed in a three-dimensional printer and is cured via a UV light source;

controlling, by the processor, a laser to heat a point of a surface of a top layer of the material;

measuring, by the processor, a loss modulus value and a storage modulus value via a Rayleigh wave of the material caused by the heat;

determining, by the processor, the UV cure level of the material comprises a fully cured level based on the loss modulus value and the storage modulus value matching a known loss modulus value and a known storage modulus value of the material at a temperature associated with the heat; and generating, by the processor, a signal to display that the material is fully cured in response to the determining.

\* \* \* \* \*